(12) United States Patent
Ahlgren

(10) Patent No.: US 9,101,484 B2
(45) Date of Patent: *Aug. 11, 2015

(54) STACKABLE SPINAL SUPPORT SYSTEM

(71) Applicant: NuVasive, Inc., San Diego, CA (US)

(72) Inventor: Dan K. Ahlgren, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/915,554

(22) Filed: Jun. 11, 2013

(65) Prior Publication Data

US 2013/0274887 A1   Oct. 17, 2013

Related U.S. Application Data

(60) Continuation of application No. 11/981,858, filed on Oct. 31, 2007, now Pat. No. 8,460,384, which is a continuation of application No. 11/053,016, filed on Feb. 8, 2005, now Pat. No. 7,887,568, which is a (Continued)

(51) Int. Cl.
*A61F 2/44* (2006.01)
*A61F 2/46* (2006.01)
(Continued)

(52) U.S. Cl.
CPC .............. *A61F 2/442* (2013.01); *A61F 2/4455* (2013.01); *A61F 2/4611* (2013.01);
(Continued)

(58) Field of Classification Search
CPC ......... A61F 2/44; A61F 2/442; A61F 2/4455; A61F 2/447; A61F 2/46; A61F 2/4611
USPC .............................. 606/105; 623/17.11–17.16
See application file for complete search history.

(56) References Cited

U.S. PATENT DOCUMENTS 3,486,505 A    12/1969  Morrison
3,518,993 A    7/1970   Blake
(Continued)

FOREIGN PATENT DOCUMENTS

CA    2015507    1/1999
EP     369603    5/1990
(Continued)

OTHER PUBLICATIONS

Request for Inter Partes Reexamination of U.S. Patent No. 7,887,568 and Exhibits G-N filed Feb. 15, 2011.

(Continued)

*Primary Examiner* — Anu Ramana
(74) *Attorney, Agent, or Firm* — Jonathan Spangler; Jennifer Russell

(57) ABSTRACT

A system for distracting two tissue surfaces away from one another within a spine, involving a plurality of biocompatible and generally rectangular spinal inserts configured to be successively stacked within a spine to distract the two tissues surfaces away from one another. Each spinal insert has a generally planar top surface having a leading edge and a trailing edge, a generally planar bottom surface disposed generally parallel to the top surface and including a leading edge and a trailing edge, and a beveled surface extending from at least one of the leading edge of the planar top surface and the leading edge of the planar bottom surface. The beveled surface is configured to allow a currently inserted spinal insert to be positioned at least one of above and below a previously introduced spinal insert to distract the two tissue surfaces.

7 Claims, 15 Drawing Sheets

Related U.S. Application Data division of application No. 09/904,179, filed on Jul. 11, 2001, now Pat. No. 6,852,126.

(60) Provisional application No. 60/218,975, filed on Jul. 17, 2000.

(51) Int. Cl.
 *A61B 17/02* (2006.01)
 *A61F 2/30* (2006.01)

(52) U.S. Cl.
 CPC ............ *A61B 2017/0256* (2013.01); *A61F 2002/30176* (2013.01); *A61F 2002/30179* (2013.01); *A61F 2002/30331* (2013.01); *A61F 2002/30504* (2013.01); *A61F 2002/30594* (2013.01); *A61F 2002/30599* (2013.01); *A61F 2002/30604* (2013.01); *A61F 2002/30828* (2013.01); *A61F 2002/448* (2013.01); *A61F 2002/4635* (2013.01); *A61F 2220/0025* (2013.01); *A61F 2220/0033* (2013.01); *A61F 2230/0054* (2013.01); *A61F 2230/0058* (2013.01); *A61F 2250/0063* (2013.01); *A61F 2310/00011* (2013.01)

(56) References Cited

U.S. PATENT DOCUMENTS

| | | |
|---|---|---|
| 3,604,487 A | 9/1971 | Gilbert |
| 3,745,995 A | 7/1973 | Kraus |
| 3,848,601 A | 11/1974 | Ma et al. |
| 4,026,304 A | 5/1977 | Levy |
| 4,026,305 A | 5/1977 | Brownlee et al. |
| 4,646,738 A | 3/1987 | Trott |
| 4,657,550 A | 4/1987 | Daher |
| 4,743,256 A | 5/1988 | Brantigan |
| 4,781,591 A | 11/1988 | Allen |
| 4,834,757 A | 5/1989 | Brantigan |
| 4,877,020 A | 10/1989 | Vich |
| 4,878,915 A | 11/1989 | Brantigan |
| 4,932,975 A | 6/1990 | Main et al. |
| 4,961,740 A | 10/1990 | Ray et al. |
| 4,962,766 A | 10/1990 | Herzon |
| 5,026,373 A | 6/1991 | Ray et al. |
| 5,055,104 A | 10/1991 | Ray |
| 5,062,845 A | 11/1991 | Kuslich et al. |
| 5,092,572 A | 3/1992 | Litwak et al. |
| 5,133,717 A | 7/1992 | Chopin |
| 5,133,755 A | 7/1992 | Brekke |
| 5,171,278 A | 12/1992 | Pisharodi |
| 5,192,327 A | 3/1993 | Brantigan |
| 5,217,497 A | 6/1993 | Mehdian |
| 5,269,785 A | 12/1993 | Bonutti |
| 5,284,153 A | 2/1994 | Raymond et al. |
| 5,290,494 A | 3/1994 | Coombes et al. |
| 5,300,076 A | 4/1994 | Leriche |
| 5,304,210 A | 4/1994 | Crook |
| 5,306,307 A | 4/1994 | Senter et al. |
| 5,306,309 A | 4/1994 | Wagner et al. |
| 5,322,505 A | 6/1994 | Krause et al. |
| 5,334,205 A | 8/1994 | Cain |
| 5,336,223 A | 8/1994 | Rogers |
| 5,364,400 A | 11/1994 | Rego, Jr. et al. |
| 5,395,372 A | 3/1995 | Holt et al. |
| 5,397,363 A | 3/1995 | Gelbard |
| 5,405,391 A | 4/1995 | Hednerson et al. |
| 5,413,602 A | 5/1995 | Metz-Stavenhagen |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen et al. |
| 5,445,639 A | 8/1995 | Kuslich et al. |
| 5,454,811 A | 10/1995 | Huebner |
| 5,458,638 A | 10/1995 | Kuslich et al. |
| 5,489,308 A | 2/1996 | Kuslich et al. |
| 5,522,879 A | 6/1996 | Scopelianos |
| 5,522,899 A | 6/1996 | Michelson |
| 5,524,624 A | 6/1996 | Tepper et al. |
| 5,527,312 A | 6/1996 | Ray |
| 5,534,030 A | 7/1996 | Navarro et al. |
| 5,540,688 A | 7/1996 | Navas |
| 5,545,222 A | 8/1996 | Bonutti |
| 5,562,736 A | 10/1996 | Ray et al. |
| 5,565,005 A | 10/1996 | Erickson et al. |
| 5,571,190 A | 11/1996 | Ulrich |
| 5,571,192 A | 11/1996 | Schonhoffer |
| 5,593,409 A | 1/1997 | Michelson |
| 5,609,636 A | 3/1997 | Kohrs et al. |
| 5,611,800 A | 3/1997 | Davis et al. |
| 5,611,810 A | 3/1997 | Arnold et al. |
| 5,632,747 A | 5/1997 | Scarborough et al. |
| 5,645,598 A | 7/1997 | Brosnahan et al. |
| 5,653,761 A | 8/1997 | Pisharodi |
| 5,653,762 A | 8/1997 | Pisharodi |
| 5,658,336 A | 8/1997 | Pisharodi |
| 5,658,337 A | 8/1997 | Kohrs et al. |
| 5,662,710 A | 9/1997 | Bonutti |
| 5,665,122 A | 9/1997 | Kambin |
| 5,669,909 A | 9/1997 | Zdeblick et al. |
| 5,676,703 A | 10/1997 | Gelbard |
| 5,683,394 A | 11/1997 | Rinner |
| 5,683,400 A | 11/1997 | McGuire |
| 5,683,464 A | 11/1997 | Wagner et al. |
| 5,690,629 A | 11/1997 | Asher et al. |
| 5,700,264 A | 12/1997 | Zucherman et al. |
| 5,700,291 A | 12/1997 | Kuslich et al. |
| 5,700,292 A | 12/1997 | Margulies |
| 5,702,449 A | 12/1997 | McKay |
| 5,702,451 A | 12/1997 | Biedermann et al. |
| 5,702,453 A | 12/1997 | Rabbe et al. |
| 5,702,454 A | 12/1997 | Baumgartner |
| 5,702,455 A | 12/1997 | Saggar |
| 5,703,451 A | 12/1997 | Yamamichi et al. |
| 5,707,373 A | 1/1998 | Sevrain et al. |
| 5,711,957 A | 1/1998 | Patat et al. |
| 5,716,415 A | 2/1998 | Steffee |
| 5,720,748 A | 2/1998 | Kuslich et al. |
| 5,720,751 A | 2/1998 | Jackson |
| 5,741,261 A | 4/1998 | Moskovitz et al. |
| 5,755,797 A | 5/1998 | Baumgartner |
| 5,766,252 A | 6/1998 | Henry et al. |
| 5,772,661 A | 6/1998 | Michelson |
| 5,775,331 A | 7/1998 | Raymond et al. |
| 5,779,642 A | 7/1998 | Nightengale |
| 5,782,830 A | 7/1998 | Farris |
| 5,782,919 A | 7/1998 | Zdeblick et al. |
| 5,785,710 A | 7/1998 | Michelson |
| 5,797,909 A | 8/1998 | Michelson |
| 5,800,549 A | 9/1998 | Bao et al. |
| 5,800,550 A | 9/1998 | Sertich |
| 5,814,084 A | 9/1998 | Grivas et al. |
| 5,851,208 A | 12/1998 | Trott |
| 5,860,977 A | 1/1999 | Zucherman et al. |
| 5,865,845 A | 2/1999 | Thalgott |
| 5,865,848 A | 2/1999 | Baker |
| 5,885,299 A | 3/1999 | Winslow et al. |
| 5,888,219 A | 3/1999 | Bonutti |
| 5,888,224 A | 3/1999 | Beckers et al. |
| 5,893,890 A | 4/1999 | Pisharodi |
| 5,899,939 A | 5/1999 | Boyce et al. |
| 5,904,719 A | 5/1999 | Errico et al. |
| 5,910,315 A | 6/1999 | Stevenson et al. |
| 5,954,769 A | 9/1999 | Rosenlicht |
| 5,968,098 A | 10/1999 | Winslow |
| 5,989,289 A | 11/1999 | Coates et al. |
| 5,993,474 A | 11/1999 | Ouchi |
| 6,004,326 A | 12/1999 | Castro et al. |
| 6,015,436 A | 1/2000 | Schunhuffer |
| 6,033,405 A | 3/2000 | Winslow et al. |
| 6,039,761 A | 3/2000 | Li et al. |
| 6,042,582 A | 3/2000 | Ray |
| 6,045,580 A | 4/2000 | Scarborough et al. |
| 6,048,342 A | 4/2000 | Zucherman et al. |

(56) References Cited

U.S. PATENT DOCUMENTS

| | | | |
|---|---|---|---|
| 6,063,088 A | 5/2000 | Winslow | |
| 6,083,225 A | 7/2000 | Winslow et al. | |
| 6,096,080 A | 8/2000 | Nicholson et al. | |
| 6,102,948 A | 8/2000 | Brosnahan, III | |
| 6,106,557 A * | 8/2000 | Robioneck et al. | 623/17.15 |
| 6,113,638 A * | 9/2000 | Williams et al. | 128/898 |
| 6,120,506 A | 9/2000 | Kohrs et al. | |
| 6,132,472 A | 10/2000 | Bonutti | |
| 6,156,038 A | 12/2000 | Zucherman et al. | |
| 6,159,211 A | 12/2000 | Boriani et al. | |
| 6,159,215 A | 12/2000 | Urbahns et al. | |
| 6,174,311 B1 | 1/2001 | Branch et al. | |
| 6,193,756 B1 | 2/2001 | Studer et al. | |
| 6,200,347 B1 | 3/2001 | Anderson et al. | |
| 6,224,607 B1 | 5/2001 | Michelson | |
| 6,224,631 B1 | 5/2001 | Kohrs | |
| 6,241,769 B1 | 6/2001 | Nicholson et al. | |
| 6,241,771 B1 | 6/2001 | Gresser et al. | |
| 6,251,140 B1 | 6/2001 | Marino et al. | |
| 6,258,125 B1 | 7/2001 | Paul et al. | |
| 6,277,149 B1 | 8/2001 | Boyle et al. | |
| 6,319,257 B1 | 11/2001 | Carignan et al. | |
| 6,371,989 B1 | 4/2002 | Chauvin et al. | |
| 6,440,142 B1 | 8/2002 | Ralph et al. | |
| 6,442,814 B1 | 9/2002 | Landry et al. | |
| 6,454,806 B1 | 9/2002 | Cohen et al. | |
| 6,461,359 B1 * | 10/2002 | Tribus et al. | 606/247 |
| 6,527,773 B1 | 3/2003 | Lin et al. | |
| 6,595,998 B2 | 7/2003 | Johnson et al. | |
| 6,610,065 B1 | 8/2003 | Branch et al. | |
| 6,635,086 B2 | 10/2003 | Lin | |
| 6,648,895 B2 | 11/2003 | Burkus et al. | |
| 6,852,126 B2 | 2/2005 | Ahlgren | |
| 7,887,568 B2 | 2/2011 | Ahlgren | |
| 2002/0058950 A1 | 5/2002 | Winterbottom et al. | |
| 2002/0082693 A1 | 6/2002 | Ahlgren | |
| 2003/0105528 A1 | 6/2003 | Shimp et al. | |
| 2003/0149438 A1 | 8/2003 | Nichols et al. | |
| 2003/0171812 A1 | 9/2003 | Grunberg et al. | |
| 2008/0065223 A1 | 3/2008 | Ahlgren | |

FOREIGN PATENT DOCUMENTS

| | | |
|---|---|---|
| EP | 517030 | 5/1992 |
| EP | 667127 | 8/1995 |
| EP | 706876 | 4/1996 |
| EP | 716840 | 6/1996 |
| EP | 737448 | 10/1996 |
| EP | 796593 | 9/1997 |
| EP | 880938 | 2/1998 |
| EP | 809974 | 4/1998 |
| EP | 809975 | 4/1998 |
| EP | 811356 | 4/1998 |
| WO | WO-91/06261 | 5/1991 |
| WO | WO-94/04100 | 3/1994 |
| WO | WO-94/10928 | 5/1994 |
| WO | WO-95/01810 | 1/1995 |
| WO | WO-96/08205 | 3/1996 |
| WO | WO-96/17564 | 3/1996 |
| WO | WO-96/41582 | 12/1996 |
| WO | WO-97/20513 | 6/1997 |
| WO | WO-97/33525 | 9/1997 |
| WO | WO-97/37620 | 10/1997 |
| WO | WO-98/09586 | 3/1998 |
| WO | WO-98/14142 | 4/1998 |
| WO | WO-98/17208 | 4/1998 |
| WO | WO-98/25539 | 6/1998 |
| WO | WO-99/08627 | 2/1999 |
| WO | WO-99/38461 | 8/1999 |
| WO | WO-00/07527 | 2/2000 |
| WO | WO-00/45712 | 8/2000 |
| WO | WO-00/45713 | 8/2000 |
| WO | WO-01/41681 | 6/2001 |
| WO | WO-01/49333 | 7/2001 |

OTHER PUBLICATIONS

Order Denying Request for Inter Partes Reexamination of U.S. Patent No. 7,887,568 mailed Mar. 11, 2011.
Petition for Review of Denied Request for Inter Partes Reexamination of U.S. Patent No. 7,887,568 filed Apr. 4, 2011.
Dismissal of Petition for Review of Denied Request for Inter Partes Reexamination of U.S. Patent No. 7,887,568 mailed Jun. 23, 2011.
Petition for Review of Denied Request for Inter Partes Reexamination of U.S. Patent No. 7,887,568 filed Aug. 22, 2011.
Dismissal of Petition for Review of Denied Request for Inter Partes Reexamination of U.S. Patent No. 7,887,568 mailed Nov. 29, 2011.
Alleyne, et al., "Current and Future Approaches to Lumbar Disc Surgery (A Literature Review)", Medscape General Medicine, 1(1), (1999) [formerly published in Medscape Orthopaedics & Sports Medicine eJournal 1(6), 1997]. Available at: http://www.medscape.com/viewarticle/408478.
Benini, et al., "Undercutting decompression and posterior fusion with translaminar facet screw fixation in degenerative lumbar spinal stenosis: Technique and results", Neuro-Orthopedics, (1995), 159-172.
Kambin, et al., "History and current status of percutaneous arthroscopic disc surgery", Spine, 21, (1996), 57S-61S.
Stein, et al., "Percutaneous facet joint fusion: Preliminary experience", Journal of Vascular and Interventional Radiology, 4, (1993), 69-74.
Vamvanij, et al., "Surgical treatment of internal disc disruption: An outcome study of bur fusion techniques", Journal of Spinal Disorders, 4, (1998), 375-382.

* cited by examiner

FIG. 8
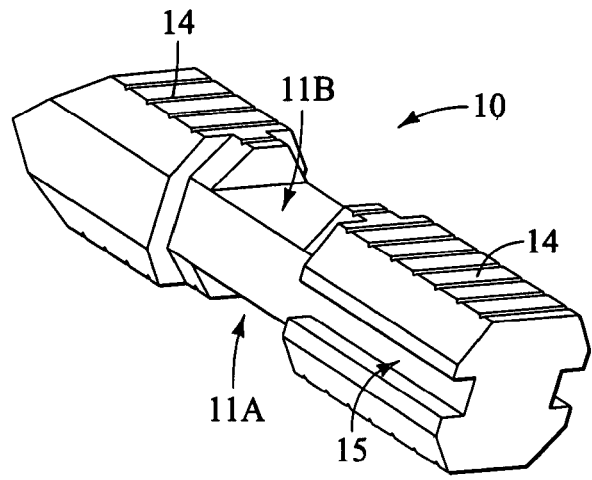
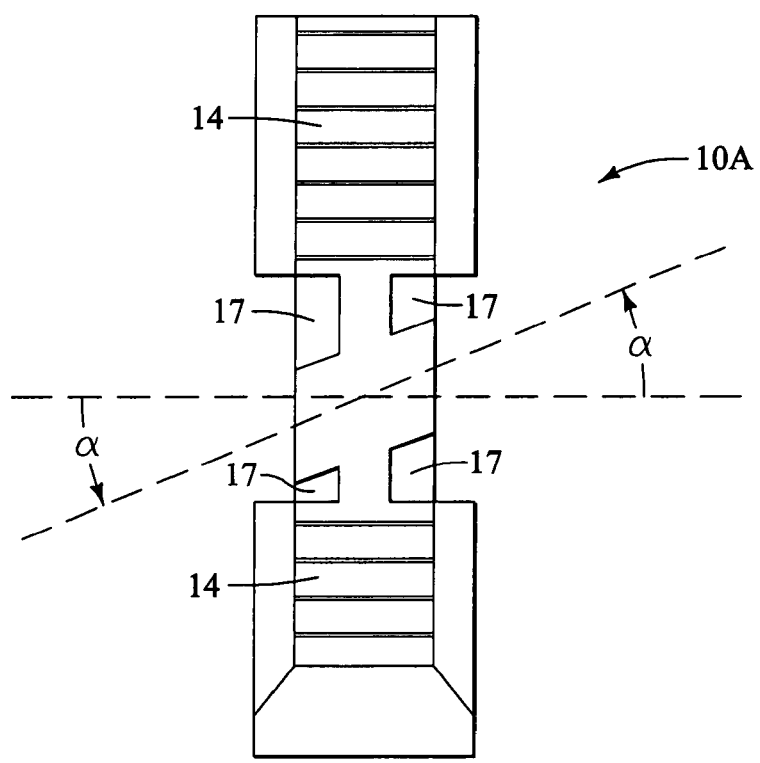
FIG. 9B

STACKABLE SPINAL SUPPORT SYSTEM

CROSS-REFERENCES TO RELATED APPLICATIONS

The present application claims priority from commonly owned and co-pending U.S. patent application Ser. No. 11/053,016, filed Feb. 8, 2005, which claims priority from U.S. patent application Ser. No. 09/904,179 filed Jul. 11, 2001, the complete disclosures of which are hereby incorporated herein by reference in their entirety for all purposes. Additionally, the present application claims benefit under 35 U.S.C. §119(e) from U.S. Provisional Application Ser. No. 60/218,975 filed Jul. 17, 2000, the entire contents of which are hereby expressly incorporated by reference into this disclosure as if set forth fully herein.

BACKGROUND OF THE INVENTION

The present invention provides a stackable interlocking intervertebral support system, and methods for supporting adjacent vertebrae using a stackable interlocking intervertebral support system.

In preferred aspects, the present invention comprises two, three (or more) separate portions which are stacked together to form an interlocked intervertebral support assembly. Advantageously, two of these three (or more) portions may be identical in size and shape, as will be explained. In the optional aspect of the invention in which only two separate portions are used, these two portions may be identical to one another in size and shape.

In one preferred aspect, the present invention preferably comprises a center portion, a top portion and a bottom portion. The top portion is positioned on top of the center portion and the bottom portion is positioned under the center portion. The top and bottom portions may be identically shaped and dimensioned, but are positioned upside down with respect to one another, on opposite sides of the center portion, as will be explained. In another aspect of the invention, however, only two portions are used, with the top portion being positioned directly on top of the bottom portion (with no center portion(s) required). In further aspects of the present invention, more than three separate portions may be used. In such aspects, a plurality of identically shaped center portions are stacked one on top of the other. In other alternate aspects, various portions (including top, center and bottom portions) may be stacked side by side one another).

In accordance with the present invention, the center portion has a recess in each of its top and bottom surfaces. Each of the top and bottom portions of the present system also have recesses therein which engage and interlock with the recesses in the center portion. More specifically, the top portion preferably has a recess in its bottom surface and the bottom portion has a recess in its top surface which engage the respective recesses in the top and bottom of the center portion.

The present invention is assembled simply by stacking the three portions (top, center & bottom) one on top of one another in a patient's intervertebral space. When stacked together, the present assembly will form an "X" or "cross" type of shape, providing support over a large surface area of the adjacent vertebrae. In further optional aspects of the invention, more than three portions are stacked together one on top of one another in a patient's intervertebral space. Specifically, a plurality of center portions are stacked on a bottom portion and a top portion is stacked thereover.

A further advantage of the present system is that, when assembled, it provides support in two perpendicular directions, thereby supporting a large area of the adjacent vertebrae, yet using only a minimal amount of material in actually achieving this advantage. This advantage is due, at least in part, to the assembled "cross" shape of the assembly. Moreover, the present invention can be dimensioned to be of a size such that the "arms" of the "cross" extend outwardly towards the edges of the vertebrae, providing support over the cortical bone at the vertebral edges.

Another advantage of the present invention is that, as the adjacent vertebrae tend to push together, this will hold the present support assembly together, even in the absence of any mechanical fastening or securing mechanisms between the top, center & bottom portions of the system. Specifically, both (one or more) center portion(s) and the two top/bottom portions are uniquely shaped and dimensioned such that when positioned one on top of another, they will remain firmly together, resisting any lateral tendency to slip apart.

Yet another advantage of the present invention is that it may be easily inserted into a patient's intervertebral space in a bi-portal minimally invasive surgical approach. Specifically, the bottom portion may be inserted through a first cannula into the patient's intervertebral space, with the center portion(s) thereafter being inserted through a second cannula into the patient's intervertebral space. The top portion may then be inserted through the first cannula into the patient's intervertebral space. In this aspect of the invention, the first and second cannulae are generally perpendicular to one another, being positioned in opposite posterolateral approaches. Alternatively, all of the portions of the assembly may be inserted through the same operating cannula into the patient's intervertebral space, with successive portions then rotated perpendicular to one another after they have been positioned in the patient's intervertebral space.

In preferred aspects, each of the center, top and bottom portions of the assembly have a tapered end, which is dimensioned to engage a ramping structure disposed within one of the recesses on an adjacent portion such that the separate portions of the assembly may be "slip-fit" together, with pressure between the adjacent vertebrae holding each of the pieces of the assembly together. In addition, an optional tapered front end of the center portion may be used to pry apart the adjacent vertebrae, prior to positioning the top portion thereover.

In optional aspects of the invention, a plurality of the present support assemblies can be positioned in a patient's intervertebral space, either on top of, beside, or both on top of and beside, one another.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 8 is a rear perspective view of the center portion of the present system;

FIG. 9B corresponds to FIG. 9A, but has center ramp/recesses angled to a lateral axis across the center portion;

DETAILED DESCRIPTION OF THE PREFERRED EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The stackable interlocking intervertebral support system disclosed herein boasts a variety of inventive features and components that warrant patent protection, both individually and in combination.

Figure 1:
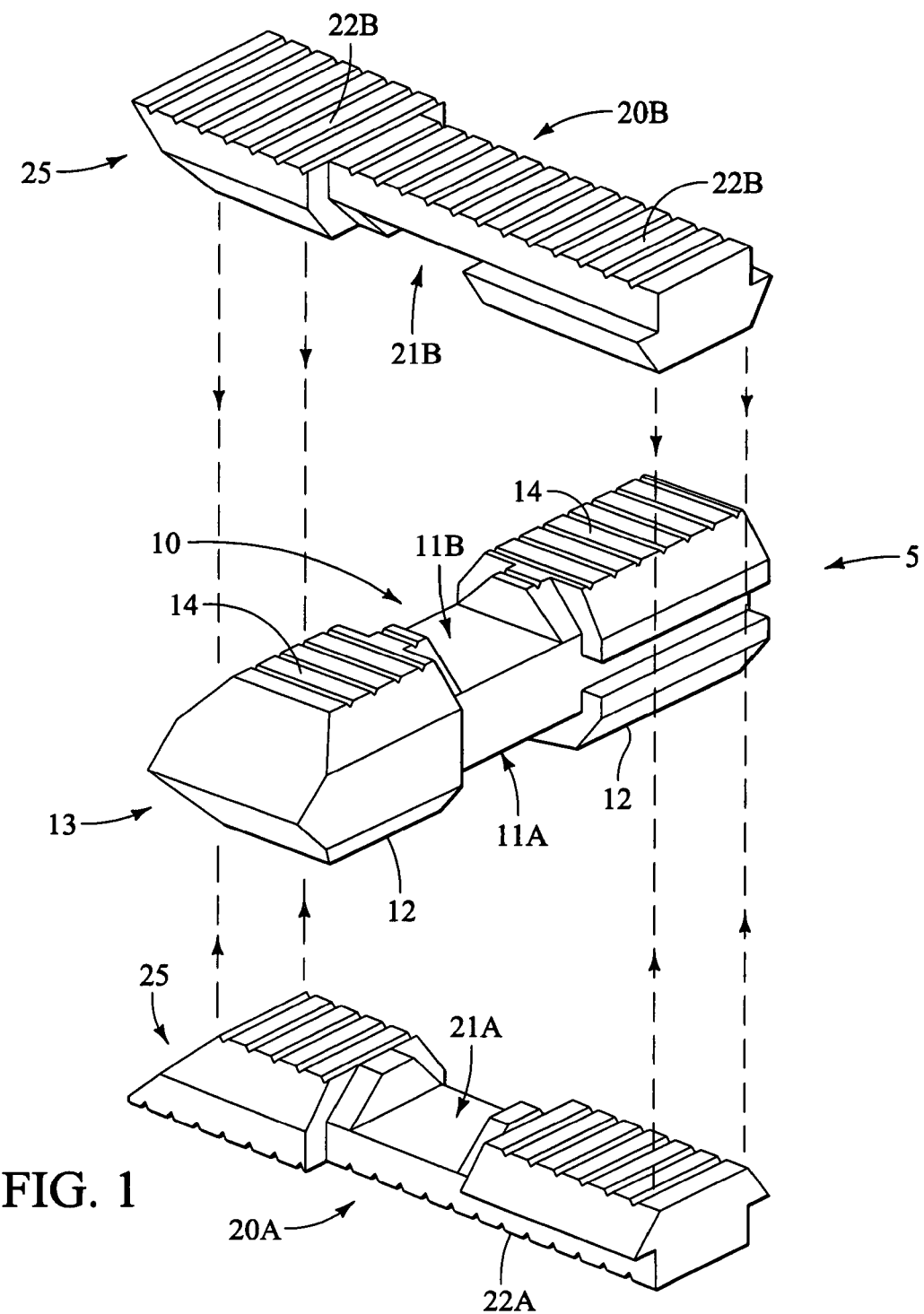
FIG. 1 is an exploded front/side perspective view of an exemplary arrangement of the present stackable interlocking intervertebral support system.

Referring first to FIG. 1, an exploded front side perspective view of the present stackable interlocking intervertebral support system 5 is provided. In one preferred arrangement, system 5 comprises a center portion 10, a bottom portion 20A and a top portion 2013. (As will be explained, other arrangements are possible). As can be seen throughout the attached Figs., portions 20A and 20B may preferably be identical in shape and size. Accordingly, the present system 5 may actually comprise one center portion 10 and two top/bottom portions 20.

Figure 2:
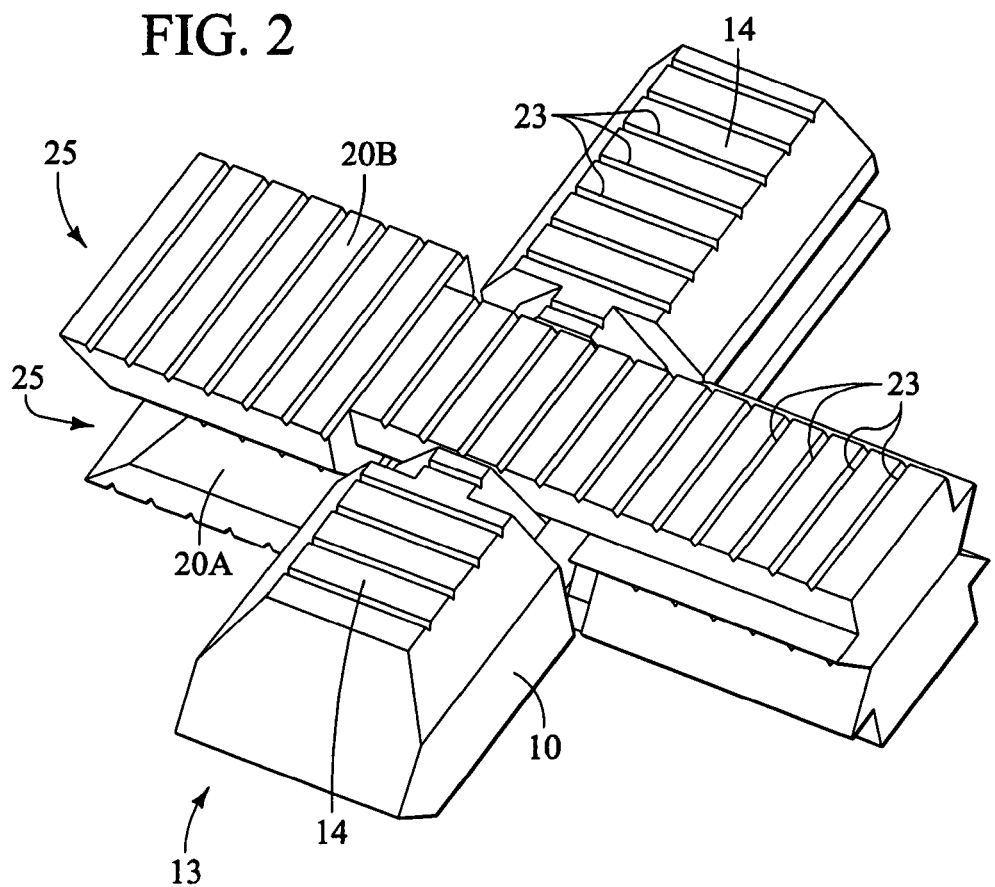
FIG. 2 is a top front/side perspective view of the exemplary arrangement of the present system seen in FIG. 1.
Figure 3:
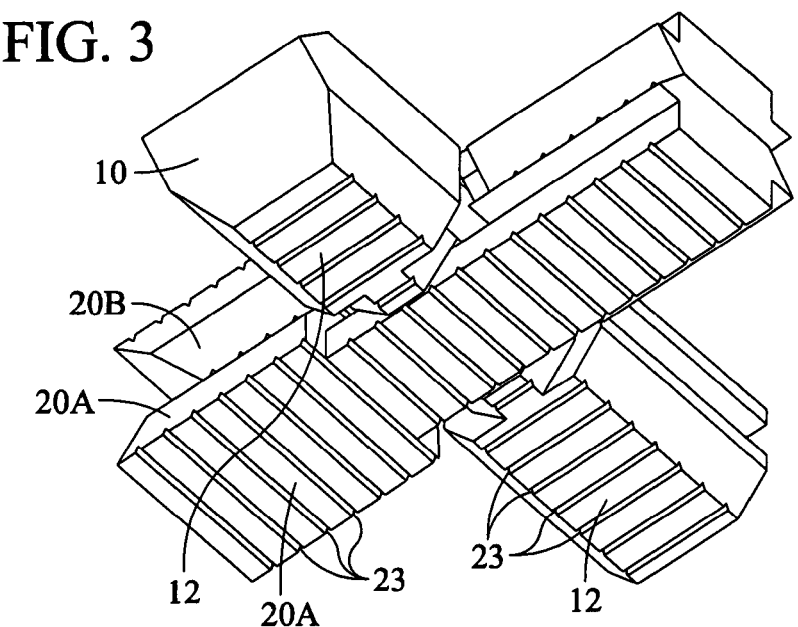
FIG. 3 is a bottom front/side perspective view of the exemplary arrangement of the present system seen in FIG. 1.
Figure 4:
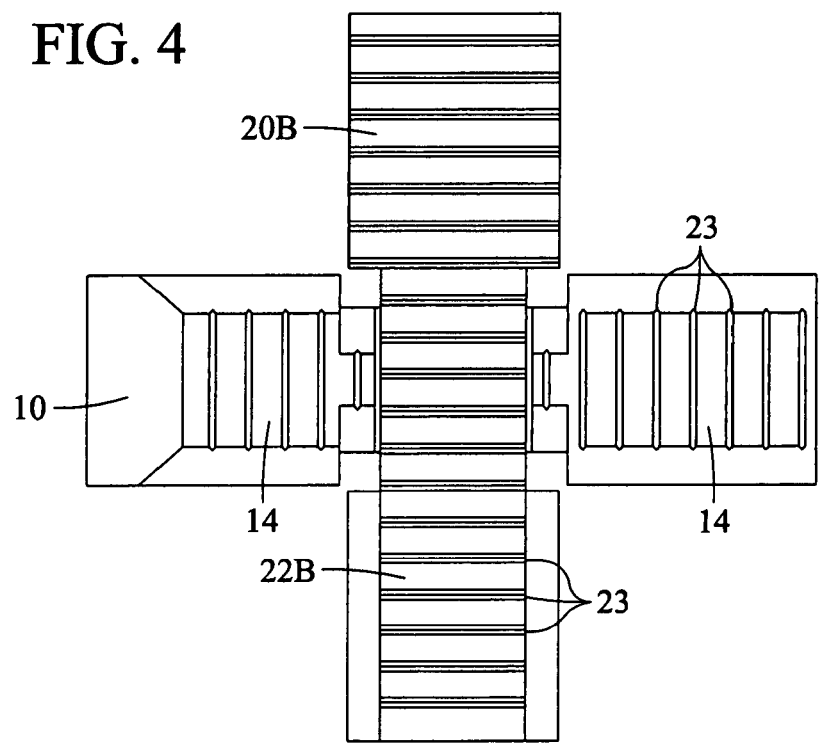
FIG. 4 is a top plan view of the exemplary arrangement of the present system seen in FIG. 1.

FIGS. 2 and 3 show respective top and bottom perspective views of the present system, in an assembled format. As will be explained, an advantage of the present system is that it provides support between adjacent vertebrae without requiring any mechanical fastening systems between the top, center and bottom portions of the assembly. Rather, center portion 10, bottom portion 20A and top portion 20B are all assembled together with their novel shapes assisting in keeping them together.

Referring to the attached Figs., (and to FIGS. 7A to 10 in particular), center portion 10 is provided with bottom recess 11A and top recess 11B, passing thereacross, as shown. Also referring to the attached Figs., (and to FIGS. 13 to 16 in particular), bottom portion 20A is also proved with a top recess 21A. (Conversely, being identically shaped to bottom portion 20A, top portion 20B is also provided with a bottom recess 21B).

An important aspect of the present invention is that, when bottom portion 20A is positioned below center portion 10, recess 21A will engage and interlock with recess 11A. Conversely, when top portion 208 is positioned on top of center portion 10, recess 218 will engage and interlock with recess 11B. Accordingly, when center portion 10, bottom portion 20A and top portion 20B are stacked together, recesses 11 will engage recesses 21, such that assembly 5 forms an "X" or "cross" shape. As can be seen, recesses 11 and 21 are preferably positioned mid-way (ie: centrally) along the respective lengths of portions 10 and 20. As illustrated, assembly 5 will have an "X" shape with each of the four branches of the "X" being relatively equal in length. Within the scope of the present invention, however, recesses 11 and 21 may instead be positioned closer to one end of their respective portions than another, such that the "X" shape of the present assembly will instead have two of its branches longer than another two of its branches (and may even approach a "V" shape assembly). Moreover, the angles at which recesses 11 and 21 cut laterally across portions 10 and 20 can be angled as denoted by angle "α" in FIG. 9B (for center portion 10). As such, when stacked together, the angles between each of the 4 "arms" of the "X" of the present assembly need not be perpendicular to one another. (For example, 2 pairs of arms may be 60° apart, with the other 2 pairs of arms being 120° apart).

Figure 5:
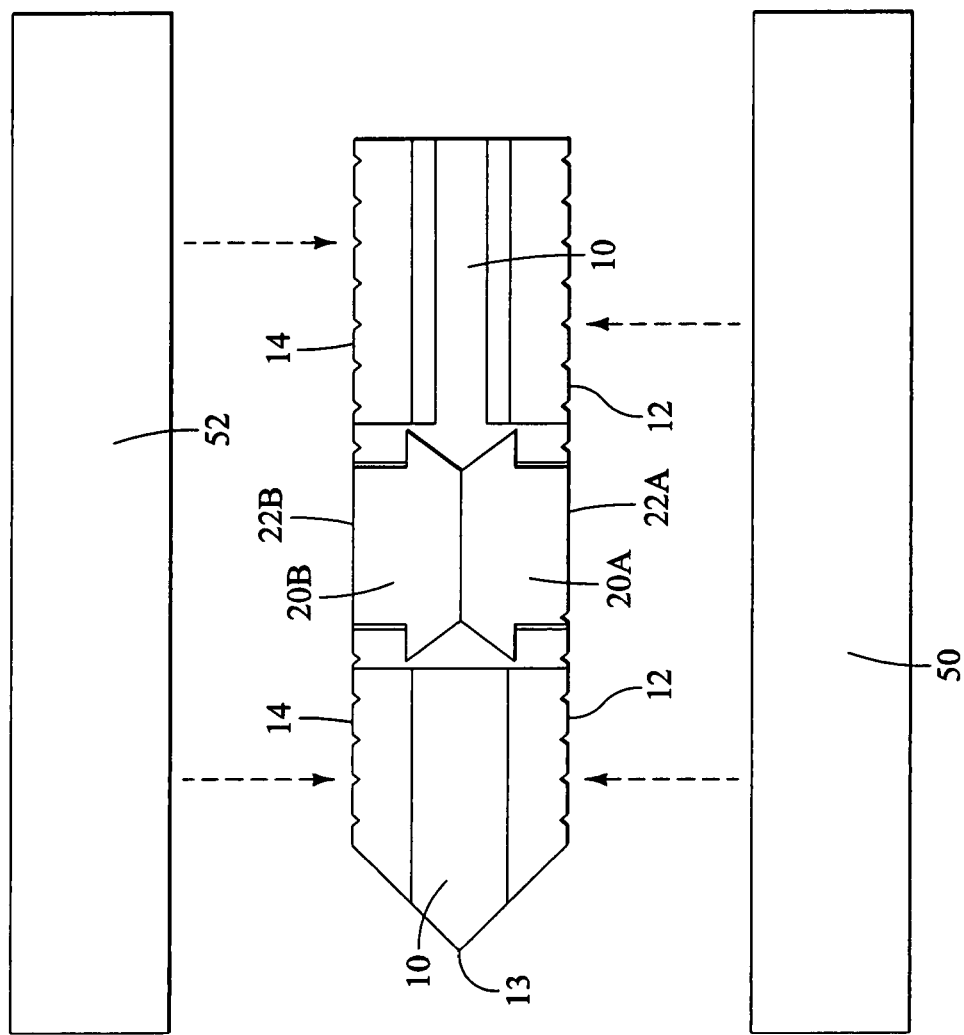
FIG. 5 is a front/side elevation view of the exemplary arrangement of the present system seen in FIG. 1, (shown in two adjacent vertebrae in an exploded view)
Figure 6:
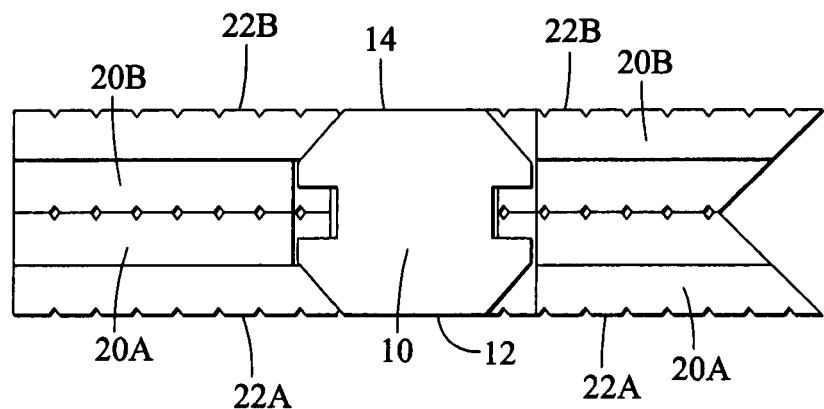
FIG. 6 is a rear elevation view of the exemplary arrangement of the present system seen in FIG. 1.

As can be seen throughout the attached Figs., center portion 10 has a bottom surface 12 and a top surface 14. Bottom portion 20A has a bottom surface 22A, and top portion 2013 has a top surface 22B. When the three portions of the present assembly are assembled, surface 14 is coplanar with surface 22B and surface 12 is coplanar with surface 22A. As shown in FIG. 5, surfaces 12 and 22A together support (ie: buttress against) vertebra 50 and surfaces 14 and 22B together support (ie: buttress against) an opposite adjacent vertebra 52. (For illustration purposes only, opposite adjacent vertebrae 50 and 52 are shown in an exploded view). It is to be understood that after distraction vertebrae 50 and 52 will tend to move toward one another, applying pressure to the top and bottom of assembly 5, keeping assembly 5 together. As can be seen, surfaces 12, 14, 22A, and 22B may all have a plurality of small groves 23 (or other surface irregularities) which increases sliding friction across these surfaces.

Figure 18:
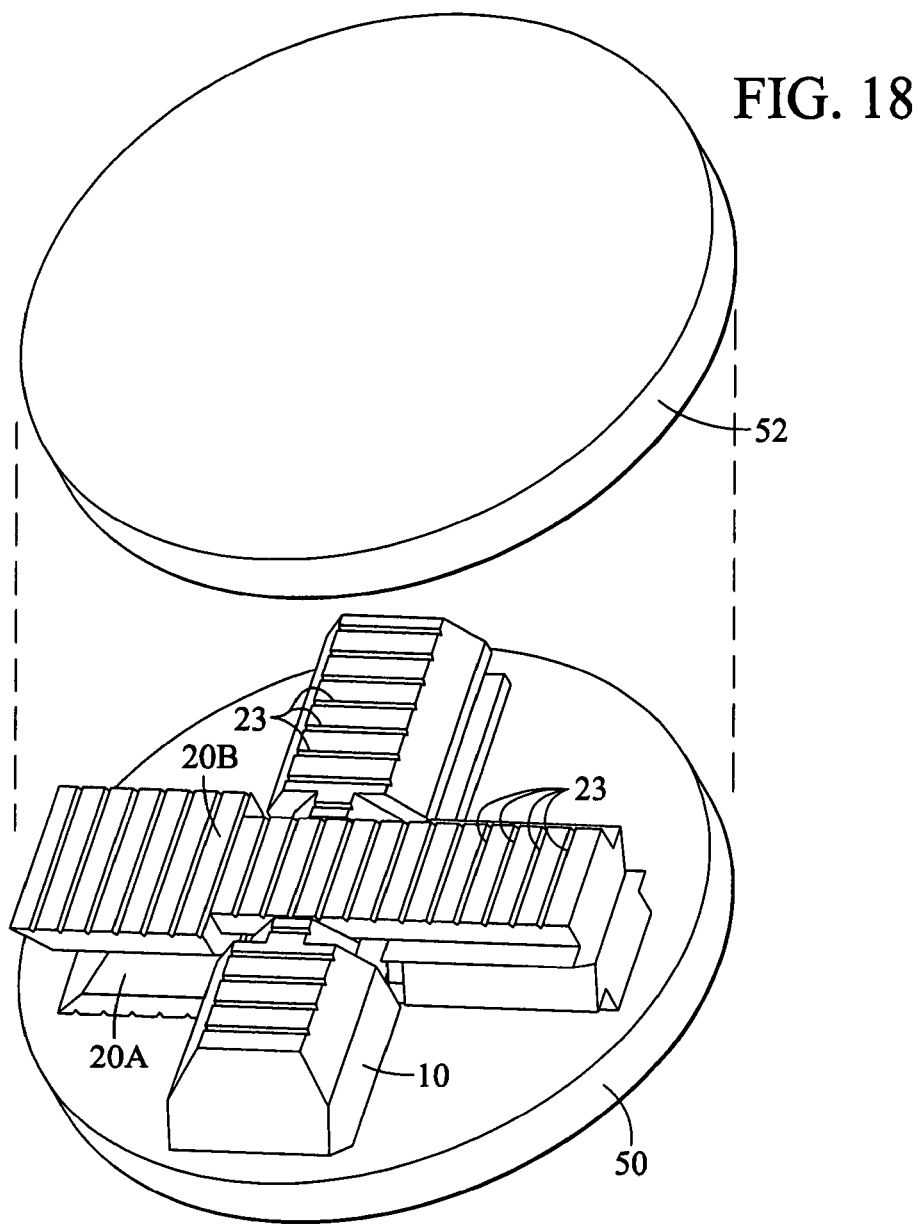
FIG. 18 is a top perspective view of a patient's intervertebral space showing the positioning of the present system (with one vertebra shown in phantom)
Figure 19:
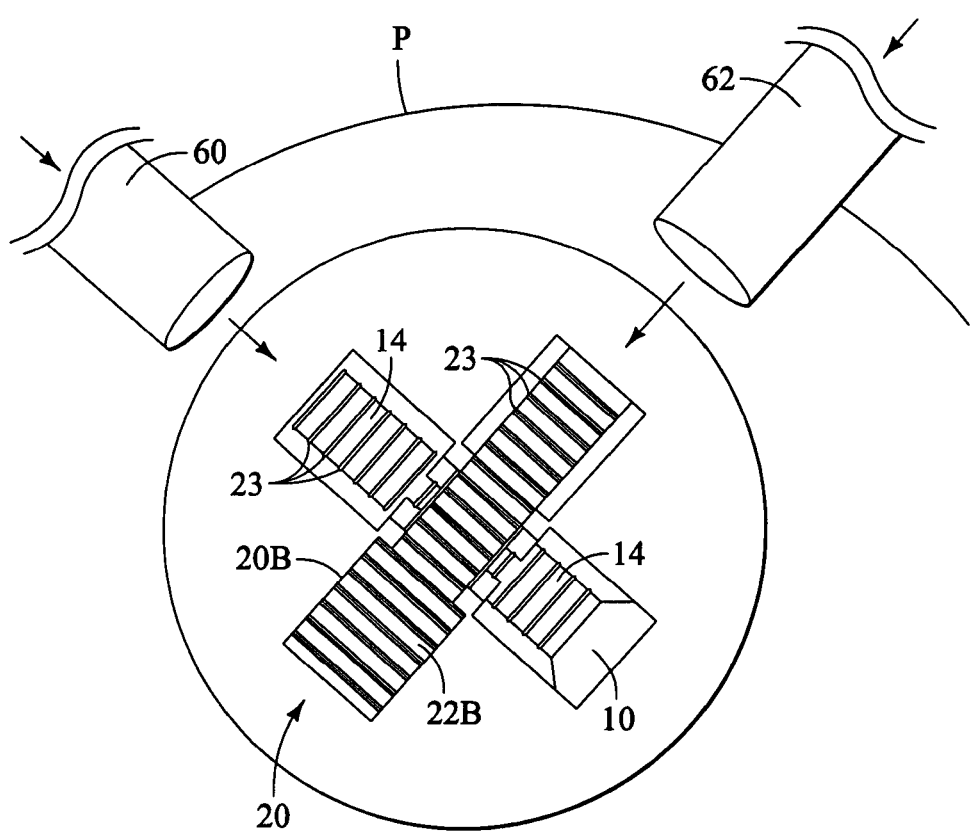
FIG. 19 is a top plan view of a patient's intervertebral space showing postero lateral approaches used in positioning the separate portions of the present system.

A further advantage of the novel shape of center portion 10 is that it has a tapered front end 13. In a preferred method of assembling the present support assembly 5, as illustrated in FIGS. 18 and 19, center portion 10 is advanced minimally invasively into patient P in a posterolateral approach through cannula 60 and positioned between opposite adjacent vertebrae 50 and 52 (shown here as being on top of vertebra 50). Tapered end 13 will tend to pry apart adjacent vertebrae 50 and 52, providing the surgeon with a "self-distracting" vertebral support system. Bottom portions 20A and top portions 20B are advanced through minimally invasive cannula 62 in an opposite posterolateral approach. Typically, bottom portion 20A is positioned first, followed by center portion 10 and top portion 20B stacked sequentially thereover.

Each of center portion 10 and top portion 20B also have tapered front ends 13 and 25 which (as center portion 10 and top portion 20B are sequentially slipped over bottom portion 10 and center portion 10), will engage ramp structures 17 disposed within recesses 21A and 11A in respective bottom portion 20A and center portion 10, such that center portion 10 and top portion 20B are "snap-fitted" over bottom portion 20A. More specifically, during insertion, vertebrae 50 and 52 will tend to rest against surfaces 12 and 14 of center portion 10. As center portion (s) 10 and top portion 20B are "snap-fitted" over bottom portion 20A and center portion 10, their respective tapered ends 13 and 25 will assist in urging vertebrae 50 and 52 apart. When assembled, ramp structures 27 disposed within recesses 21A and 21B will interlock with engage ramp structures 17 in center portion 10, such that assembly 5 will be held together, by intervertebral pressure (on surfaces 14 and 22B, and surfaces 12 and 22A) urging vertebrae 50 and 52 together.

Portions 10 and 20 of the present invention may preferably each have a narrow elongated shape, as shown. Accordingly, they may be dimensioned to be small enough to pass through an operating cannula, for example, an operating cannula having an interior diameter equal to, or less than, 8 mm or 6 mm.

Figure 7A:
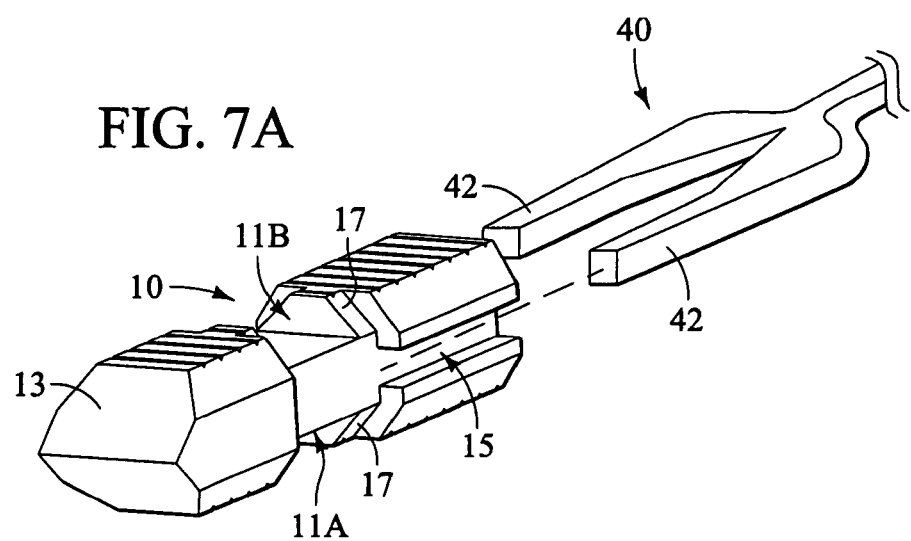
FIGS. 7A, 7B and 7C are front perspective views of the center portion of the present system.
Figure 7B:
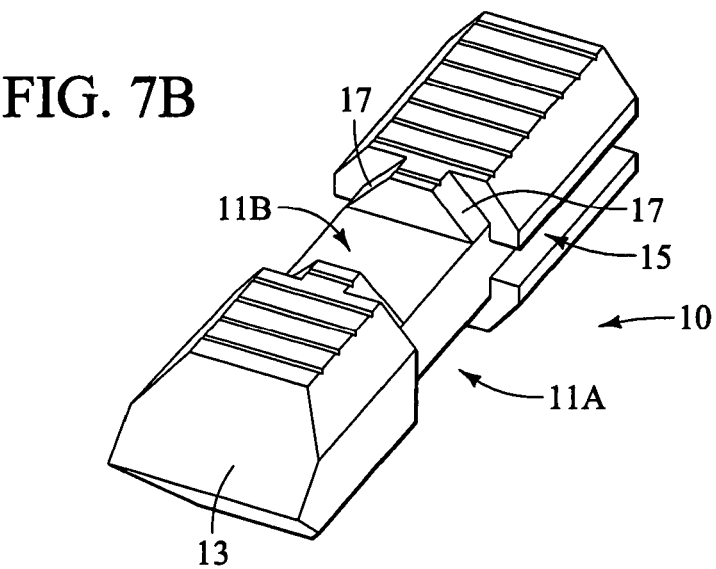
Figure 7C:
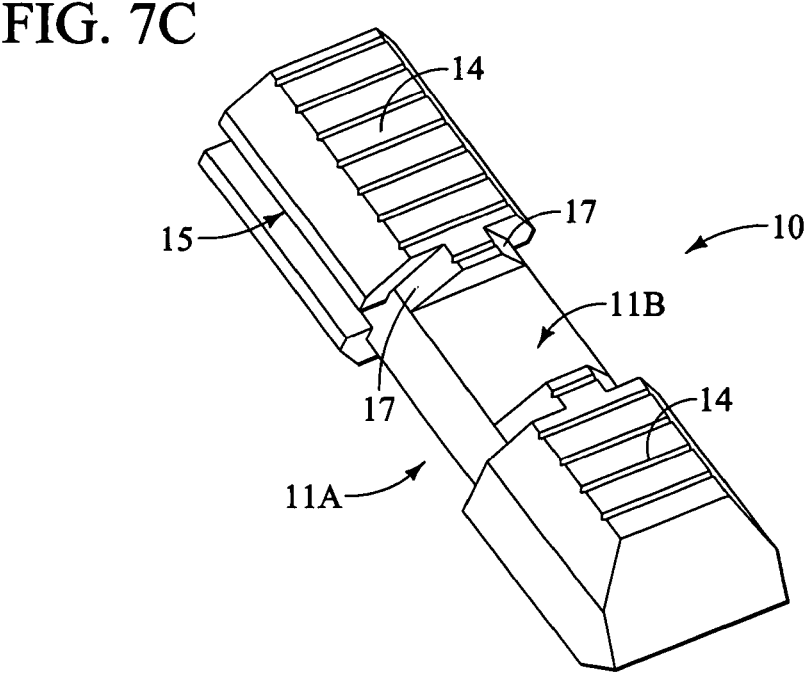
Figure 9A:
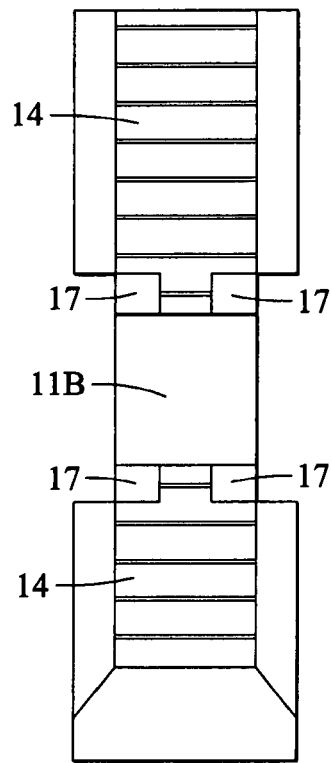
FIG. 9A is a top plan view of the center portion of the present system.
Figure 10:
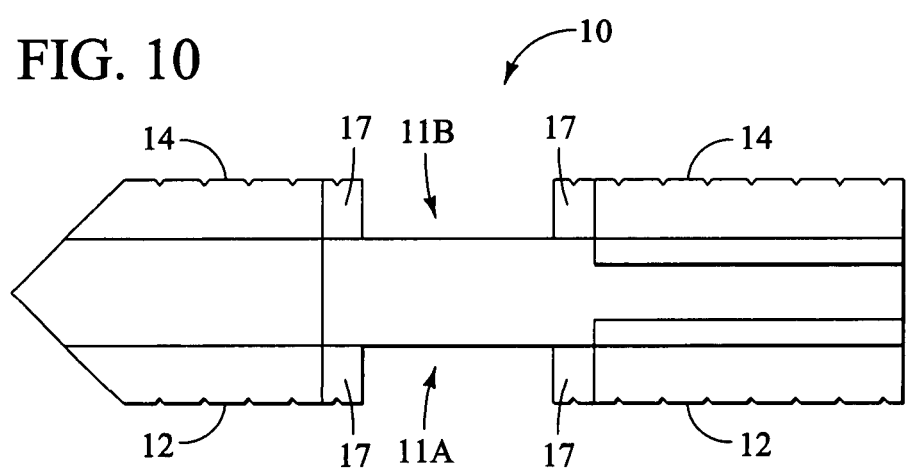
FIG. 10 is a side elevation view of the center portion of the present system.
Figure 11:
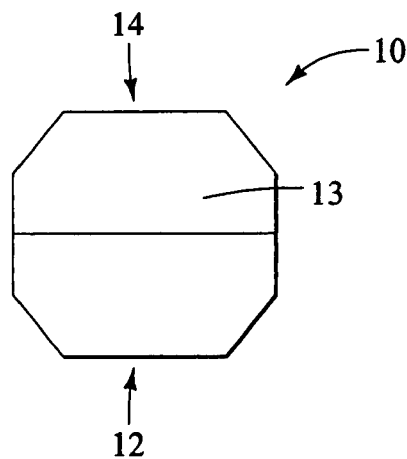
FIG. 11 is a front elevation view of the center portion of the present system.
Figure 12:
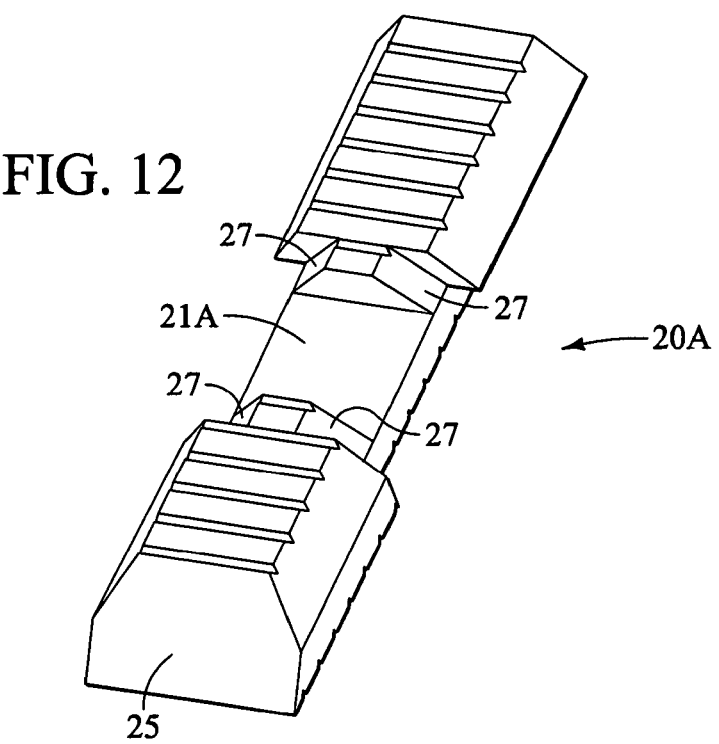
FIG. 12 is a top front perspective view of the bottom portion of the present system, (or is a bottom perspective view of the top portion of the present system)
Figure 13:
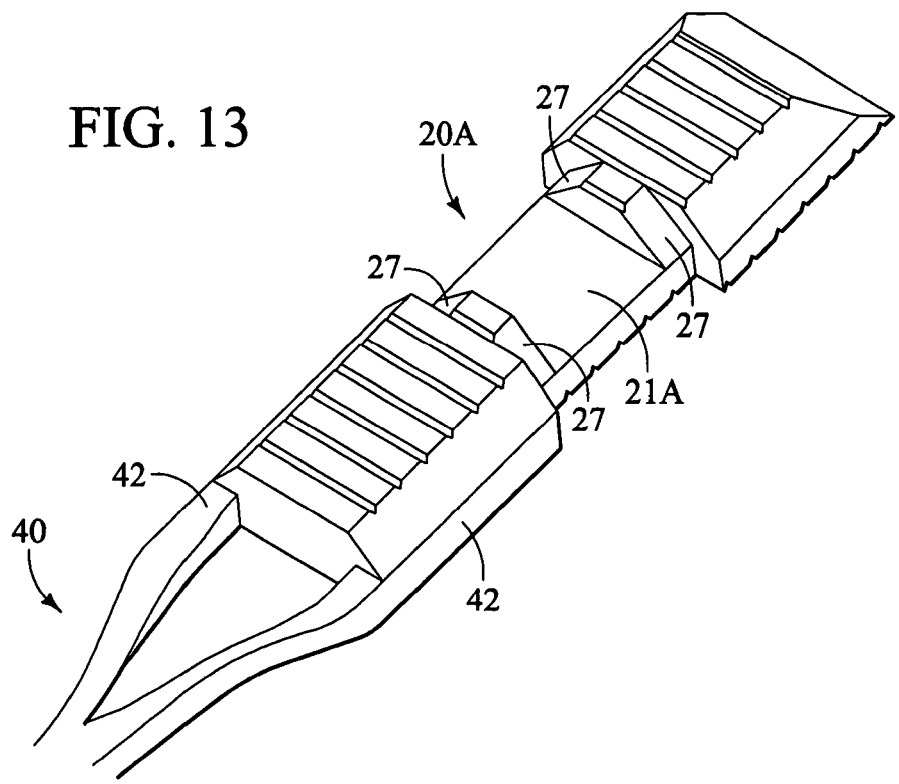
FIG. 13 is a top rear perspective view of the bottom portion of the present system, (or is a bottom perspective view of the top portion of the present system)
Figure 14:
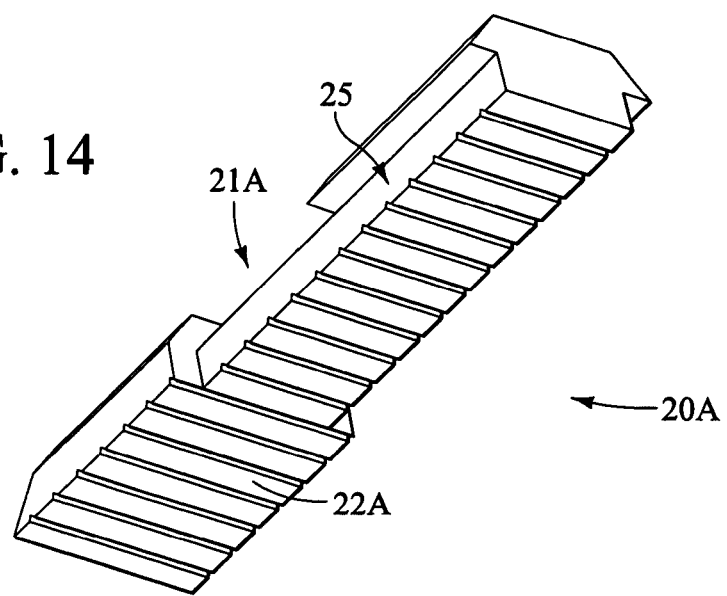
FIG. 14 is a bottom rear perspective view of the bottom portion of the present system.
Figure 15:
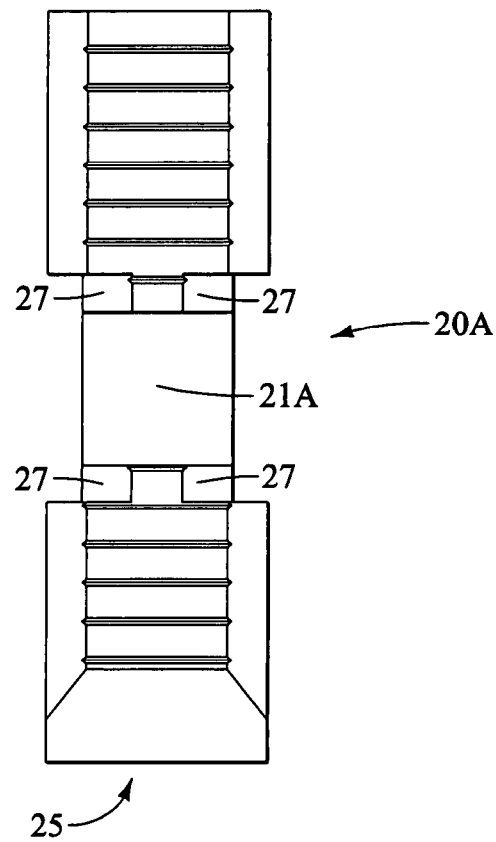
FIG. 15 is a top plan view of a bottom portion of the present system.
Figure 16:
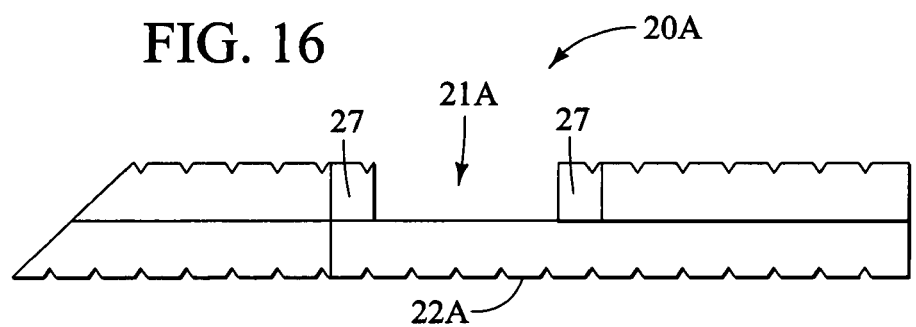
FIG. 16 is a side elevation view of the bottom portion of the present invention.
Figure 17:
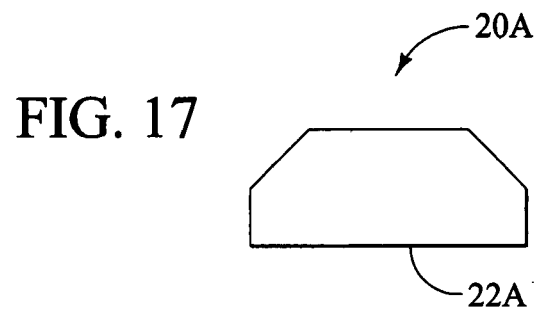
FIG. 17 is a front elevation view of the bottom portion of the present invention.

In preferred aspects of the invention, portions 10 and 20 are preferably made of bone allograft material, offering the advantages of promoting healing and eventual absorption of system 5. Alternatively, portions 10 and 20 may be made of metal, or any other suitable bio-implantable material. Each of center portion 10, and top/bottom portion 20 may optionally have side grooves 15 and 25 in which opposite prongs 42 of a two prong inserter 40 (such as a "pinching" inserter as shown in FIGS. 7A and 13) which may be used when inserting each of center portion 10 and top/bottom portions 20 through respective surgical cannulae 60 and 62.

Figure 20:
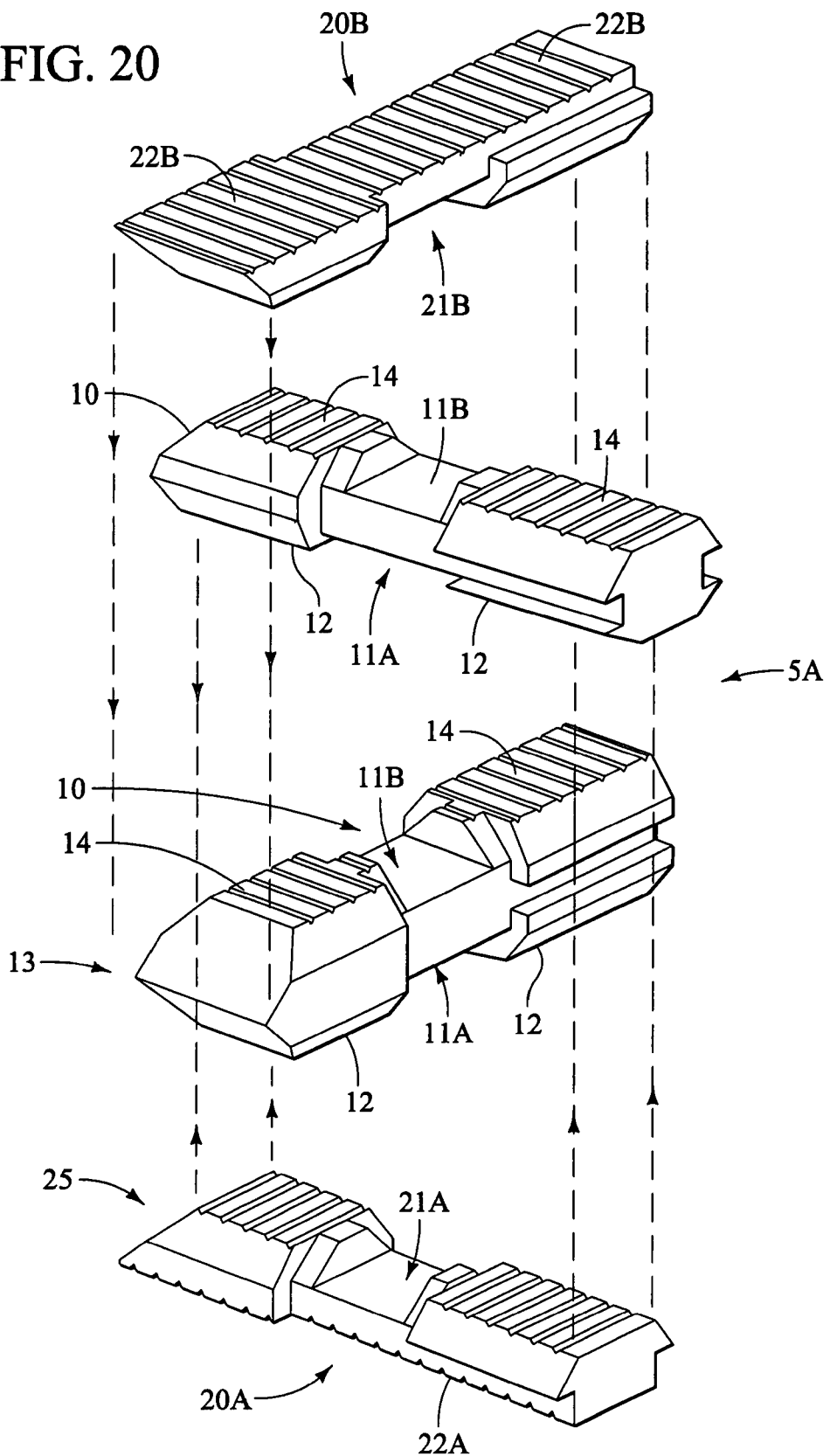
FIG. 20 is an exploded perspective view of a patient's intervertebral space showing an assembly comprising four portions, (including two center portions, a top portion and a bottom portion) positioned one on top of the other.
Figure 21:
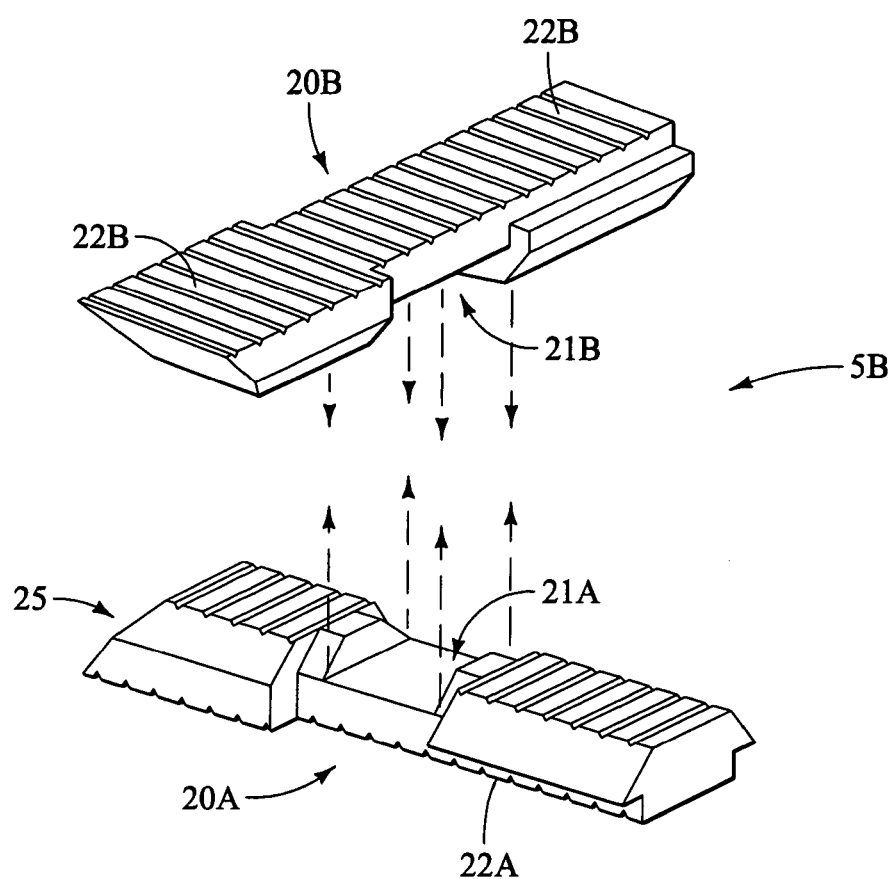
FIG. 21 is an exploded perspective view of a two-portion intervertebral support assembly.

If desired, the vertical height of the present system can be increased by stacking more than one center portion 10 (as shown in FIG. 20 in which an assembly 5A is shown having two center portions 10). It is to be understood that more than two center portions 10 may be used in assembling the present intervertebral support system, as desired. In yet another optional aspect of the invention, assemblies 5 may be made small enough such that more than one can be positioned side by side in a patient's intervertebral space. As is seen in FIG. 21, a two portion intervertebral support assembly 5B is also contemplated. In this aspect of the invention, top portion 20B is positioned directly on top of bottom portion 20A, with recesses 21A and 21B interlocking together. Many other system arrangements are possible. For example, two, or more than two portions 10 can be stacked on top of one another (similar to the stacking of portions 20 in FIG. 21).

The invention claimed is:

1. A system for distracting two tissue surfaces away from one another within a spine, comprising:
   first and second elongated biocompatible inserts, each elongated biocompatible insert having a top surface having a first leading edge and a first trailing edge, a bottom surface including a second leading edge and a second trailing edge, first and second side surfaces extending between said top and bottom surfaces, and a beveled surface extending between said first and second leading edges, said beveled surface configured to facilitate successive stacking of said elongated biocompatible inserts to distract said two tissue surfaces in said given direction during consecutive insertion into said spine, each of said inserts having a length dimension defined by the distance between one of said first and second leading edges and the corresponding one of said first and second trailing edges, a width dimension defined by the distance between said first and second side surfaces, and a height dimension defined by the distance between said top and bottom surfaces, at least one of said inserts having a solid cross-section taken along a plane generally parallel to at least one of said top and bottom surfaces, such that said length dimension is greater than said width dimension;
   wherein each of the first and second elongated biocompatible inserts is configured to be inserted into the spine one at a time such that the elongated biocompatible inserts are consecutively stacked upon one another with the spine, and such that a portion of the bottom surface of the first elongated biocompatible insert is received within a portion of the top surface of the second elongated biocompatible insert to form a structure extending in a given direction within the spine.

2. The system of claim 1, wherein each of said elongated biocompatible inserts is sized to be advanced into said space through a surgical cannula.

3. The system of claim 1, wherein each of said elongated biocompatible inserts is composed of bone allograft.

4. The system of claim 1, wherein each of said elongated biocompatible inserts include a plurality of grooves for engagement with an insertion tool.

5. The system of claim 1, wherein the beveled surface of the second elongated biocompatible insert interacts with the first elongated biocompatible insert to assist in positioning said second elongated biocompatible insert vertically adjacent to the first elongated biocompatible insert.

6. The system of claim 5, further comprising a third elongated biocompatible insert having a beveled surface, wherein the beveled surface of the third elongated biocompatible insert interacts with the second elongated biocompatible insert to assist in positioning said third elongated biocompatible insert vertically adjacent to the second elongated biocompatible insert.

7. The system of claim 1, wherein the two tissue surfaces comprise a bottom surface of a superior vertebra and a top surface of an inferior vertebra.

* * * * *